US009481886B2

(12) United States Patent
Ding et al.

(10) Patent No.: US 9,481,886 B2
(45) Date of Patent: Nov. 1, 2016

(54) RNA SILENCING IN ANIMALS AS AN ANTIVIRAL DEFENSE

(71) Applicant: The Regents of the University of California, Oakland, CA (US)

(72) Inventors: Shou-Wei Ding, Riverside, CA (US); Hong-Wei Li, Riverside, CA (US); Wan-Xiang Li, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/668,811

(22) Filed: Mar. 25, 2015

(65) Prior Publication Data
US 2015/0267203 A1 Sep. 24, 2015

Related U.S. Application Data

(63) Continuation of application No. 11/330,650, filed on Jan. 11, 2006, now abandoned, which is a continuation of application No. 10/150,283, filed on May 15, 2002, now abandoned.

(51) Int. Cl.
| | |
|---|---|
| *C07H 21/02* | (2006.01) |
| *C07H 21/04* | (2006.01) |
| *C12N 15/07* | (2006.01) |
| *C12N 7/00* | (2006.01) |
| *C12N 15/113* | (2010.01) |
| *C07K 14/005* | (2006.01) |
| *C12N 15/82* | (2006.01) |
| *C12N 15/85* | (2006.01) |
| *C12N 15/86* | (2006.01) |

(52) U.S. Cl.
CPC ......... *C12N 15/1131* (2013.01); *C07K 14/005* (2013.01); *C12N 15/8218* (2013.01); *C12N 15/85* (2013.01); *C12N 15/86* (2013.01); *C12N 2310/14* (2013.01); *C12N 2760/16122* (2013.01); *C12N 2770/30022* (2013.01); *C12N 2830/002* (2013.01)

(58) Field of Classification Search
None
See application file for complete search history.

(56) References Cited

U.S. PATENT DOCUMENTS

| 5,591,440 A | 1/1997 | Carman et al. |
| 6,204,028 B1 | 3/2001 | Ricciardi et al. |
| 6,225,048 B1 | 5/2001 | Soderberg-Naucler et al. |
| 6,291,524 B1 | 9/2001 | Huang et al. |
| 6,924,095 B2 | 8/2005 | McGrath et al. |

OTHER PUBLICATIONS

Aoki-Sei, et al., "In Vitro Inhibition of Hepatitis B Virus Replication by 2',3'-Dideoxyguanosine, 2',3'-Dideoxyinosine, and 3'-Azido-2',3'-Dideoxythymidine in 2.2.15 (PR) Cells," *J. Inf. Dis.*, vol. 164: pp. 843-851 (1991).
Agrawal, et al., "Antisense therapeutics: is it as simple as complementary base recognition?," *Molecular Med. Today*, 2000, vol. 6, pp. 72-81.
Ball, et al., "Requirements for the Self-Directed replication of flock house virus RNA 1," *J. Virol.*, 1995, vol. 69, No. 2, pp. 720-727.
Baulcombe, "Fast forward genetics based on virus-induced gene silencing," *Curr. Opin. in Plant Biol.* 1999, pp. 109-113, vol. 2.
Branch, "A good antisense molecule is hard to find," *Trends in Biochem. Sci*, 1998, vol. 23, pp. 45-50.
Brigneti, et al. "Viral pathogenicity determinants are suppressors of transgene silencing in *Nicotiana benthamiana,*" *EMBO J.* Nov. 16, 1998, pp. 6739-6746, vol. 17, No. 22.
Chen, et al., "RNA Interference Targeting VP1 Inhibits Foot-and-Mouth Disease Virus Replication in BHK-21 Cells and Suckling Mice," *Journal of Virology*, Jul. 2004, pp. 6900-6907, vol. 78, No. 13.
Chirila, et al., "The use of synthetic polymers for delivery of therapeutic antisense oligodeoxynucleotides," *Biomaterials*, 2002, vol. 23, pp. 321-342.
Corbeau, Interfering RNA and HIV: Reciprocal Interferences PLoS, vol. 9, No. 9, pp. 1-9, 2008.
Crooke, Antisense Res. & Application, 1999, Chapter 1, pp. 1-50, ed. by S. Crooke, Publ. By Springer-Verlag.
Dasgupta, et al., "Flock house virus: a simple model for studying persistent infection in cultured *Drosophila* cells," *Arch. Virol. Supplementum*, (1994) vol. 9, pp. 121-132.
Derossi, et al., "The Third Helix of the Antennapedia Homeodomain Translocates through Biological Membranes," *J. Biol. Chem.*, 1994, vol. 269, No. 14, pp. 10444-10450.
Di Serio, et al. "Sense-and antisense-mediated gene silencing in tobacco is inhibited by the same viral suppressors and is associated with accumulation of small RNAs," *PNAS USA* May 22, 2001, pp. 6506-6510, vol. 98, No. 11.
Ding, "RNA silencing," *Curr. Opin. Biotechnol.* Apr. 2000, pp. 152-156, vol. 11, No. 2.
Ding, et al., "A novel naturally occurring hybrid gene encoded by a plant RNA virus facilitates long distance virus movement," *EMBO J.* Dec. 1, 1995, pp. 5762-5772, vol. 14, No. 23.
Ding, et al., "Efficient infection from cDNA clones of cucumber mosaic cucumovirus RNAs in a new plasmid vector," *J. Gen. Virol.* Feb. 1995, pp. 459-464, vol. 76, Part 2.
Ding, et al. "New Overlapping Gene Encoded by the Cucumber Mosaic Virus Genome," *Virology*, Feb. 1994, pp. 593-601, vol. 198, No. 2.
Ding, et al., "An interspecies hybrid RNA virus is significantly more virulent than either parental virus," *Proc. Natl. Acad. Sci.*, 1996, vol. 93, pp. 7470-7474.
Elliott, et al., "Intercellular Trafficking and Protein Delivery by a Herpesvirus Structural Protein," *Cell*, vol. 88, pp. 223-233.
Eckerle, et al., "Replication of the RNA Segments of a Bipartite Viral Genome is Coordinated by a Transactivating Subgenomic RNA," *Virol.* 2002, vol. 296, pp. 165-176.

(Continued)

*Primary Examiner* — Richard Schnizer
(74) *Attorney, Agent, or Firm* — Kilpatrick Townsend & Stockton LLP

(57) ABSTRACT

The present invention provides recombinant DNA constructs for inactivation of viral or endogenous genes in a cell, wherein the construct comprises viral sequence sufficient to activate RNA silencing. In another aspect, the invention provides methods for identifying RNA silencing suppressors by sequence analysis and functional tests. In yet another aspect, the invention provides a method for identifying inhibitors of RNA silencing suppressors. In still other aspects, the invention comprises methods for identifying genes in the antiviral RNA silencing pathway, enhancers of the antiviral pathway, and methods of treating or preventing viral infections using enhancers of the pathway.

4 Claims, 4 Drawing Sheets

(56) References Cited

OTHER PUBLICATIONS

Frielle, et al, "Inhibitory effects of Vesicular Stomatitis Virus on Cellular and Influenza Viral RNA Metabolism and Protein Synthesis," *Virology*, vol. 172: pp. 274-284, 1989.

GenBank Accession U13682.1, retrieved Jan. 4, 2005, from http://www.ncbi.nlm.nih.gov/entrez/viewer.fcgi?db=nucleotide&val=541604.

Guo, H.S. and Ding, S.W. "A viral protein inhibits the long range signaling activity of the gene silencing signal," *EMBO J.* Feb. 1, 2002, pp. 398-407, vol. 21, No. 3.

Huang, et al., "Cellular microRNAs contribute to HIV-1 latency in resting primary CD4+T lymphocytes," *Nature Medicine*, vol. 13: pp. 1241-1247, 2007.

Ji, L.H. and Ding, S.W. "The suppressor of transgene RNA silencing encoded by *Cucumber mosaic* virus interferes with Salicyclic Acid-Mediated Virus Resistance," *Mol. Plant Microbe Interact*. Jun. 2001, pp. 715-724, vol. 14, No. 6.

Johansen, "Silencing on the Spot. Induction and Suppression of RNA Silencing in the *Agrobacterium*-Mediated Transient Expression System," *Plant Physiol* Jul. 2001, pp. 930-938, vol. 126, No. 3.

Jones, et al., "RNA-DNA Interactions and DNA Methylation in Post-Transcriptional Gene Silencing," *Plant Cell*. Dec. 1999, pp. 2291-2301, vol. 11, No. 12.

Lara-Pezzi, et al., The hepatitis B virus X protein promotes tumor cell invasion by inducing membrane-type matrix metalloproteinase-1 and cyclooxygenase-2 expression, *J. Clin. Invest.*, vol. 110(12): pp. 1831-1838, 2002.

Lecellier, et al., "A Cellular MicroRNA Mediates Antiviral Defense in Human Cells," *Science*, vol. 308: pp. 557-560, 2005.

Li, et al., "Strong host resistance targeted against a viral suppressor of the plant gene silencing defense mechanism," *EMBO J*. May 17, 1999, pp. 2683-2691, vol. 18, No. 10.

Li, et al., "Viral suppressors of RNA silencing," *Curr. Opin. Biotechnol*. Apr. 2001, pp. 150-154, vol. 12, No. 2.

Li, et al., "Interferon antagonist proteins of influenza and vaccinia viruses are suppressors of RNA silencing," *Proc. Natl. Acad. Sci.*, 2004, vol. 101, No. 5, pp. 1350-1355.

Li, et al., "Induction and Suppression of RNA Silencing by an Animal Virus," *Science*, vol. 296, pp. 1319-1321.

Lindenbach, et al., "RNAi Targeting an Animal Virus: News from the Front," *Mol. Cell*, 2002, vol. 9, No. 5, pp. 925-927.

Llave, et al., "Virus-encoded suppressor of posttranscriptional gene silencing targets a maintenance step in the silencing pathway," *PNAS USA* Nov. 21, 2000, pp. 13401-13406, vol. 97, No. 24.

Lu, et al., "Adenovirus VAI Noncoding RNA Can Inhibit Small Interfering RNA and MicroRNA Biogenesis," *Journal of Virology*, Dec. 2004, pp. 12868-12876., vol. 78, No. 23.

Lucy, et al., "Suppression of post-transcriptional gene silencing by a plant viral protein localized in the nucleus," *EMBO J*. Apr. 3, 2000, pp. 1672-1680, vol. 19, No. 7.

Marathe, et al., "Plant viral suppressors of post-transcritional silencing do not suppress transcriptional silencing," *Plant J.* Apr. 2000, pp. 51-59, vol. 22, No. 1.

Marathe, R. et al., "RNA viruses as inducers, suppressors and targets of post-transcriptional gene silencing," *Plant Mol. Biol*. Jun. 2000, pp. 295-306, vol. 43, Nos. 2-3.

Matzke, et al., "RNA-based silencing strategies in plants," *Curr. Opin. Genet. Dev*. Apr. 2001, pp. 221-227, vol. 11, No. 2.

Miller, et al., Flock House Virus RNA Replicates on Outer Mitochondrial Membranes in *Drosophila* Cell, *J. Virol.*, 2001, vol. 75(23): pp. 11664-11676.

Paul, et al., "Regulation of expression of the rat *SOCS*-3 gene in hepatocytes by growth hormone, interleukin-6 and glucocorticoids mRNA analysis and promoter characterization," *Eur. J. Biochem*. Oct. 2000, pp. 5849-5857, vol. 267, No. 19.

Peracchi, "Prospects for antiviral ribozymes and deoxyribozymes," *Rev. Med. Virol.*, 2004, vol. 14, pp. 47-64.

Peyman, "Mammalian Expression Cloning of Two Human Trophoblast Suppressors of Major Histocompatibility Complex Genes," *Am. J. Reprod. Immunol*. Jun. 2001, pp. 382-392, vol. 45, No. 6.

Pluymers, et al., "Nuclear Localization of Human Immunodeficiency Virus Type 1 Integrase Expressed as a Fusion Protein with Green Fluorescent Protein," *Virology*, vol. 258, pp. 327-332 (1999).

Pooga, "Cell penetration by transportan," *FASEB J*. 1998, vol. 12, pp. 67-77.

Price, et al., "DNA-Directed Expression of Functional Flock House Virus RNA1 Derivatives in *Saccharomyces cerevisiae*, Heterologous Gene Expression, and Selective Effects on Subgenomic mRNA Synthesis," *Virol.*, 2000, vol. 74, No. 24, pp. 11724-11733.

Rovere, et al., "RNA-mediated virus resistance," *Curr. Opin. in Biotechnol*. Apr. 1, 2002, pp. 167-172, vol. 13, No. 2.

Shi, et al., "In vivo expression of an overlapping gene encoded by the cucumoviruses," *J. Gen. Virol.* Jan. 1997, pp. 237-241, vol. 78, Part 1.

Shigeta, et al., "Comparative Activities of Several Nucleoside Analogs against Influenza A, B, and C viruses in Vitro.," *Antimicrob. Agents Chemother.*, vol. 32(6): pp. 906-911, 1988

Soldan, et al., "La Crosse Virus Nonstructural Protein NSs Counteracts the Effects of Short Interfering RNA," *Journal of Virology*, Jan. 2005, p. 234-244, vol. 79, No. 1.

Song, et al., "Cellular MicroRNAs Inhibit Replication of the H1N1 Influenza A Virus in Infected Cells," *Virol.*, vol. 84(17): pp. 8849-8860, 2010.

Tamm, et al., "Antisense therapy in oncology: new hope for an old idea?," *The Lancet*, 2001, vol. 358, pp. 489-497.

Tang, et al., "Gene silencing: double-stranded RNA mediated mRNA degradation and gene inactivation," *Cell Res*. Sep. 2001, pp. 181-186, vol. 11, No. 3.

Vance, et al., "RNA silencing in plants-defense and counterdefense," *Science*, Jun. 22, 2001, pp. 2277-2280, vol. 292.

Vaucheret, et al., "Post-transcriptional gene silencing in plants," *J. Cell Sci*. 2001, pp. 3083-3091, vol. 114.

Voinnet, et al. "Suppression of gene silencing: A general strategy used by diverse DNA and RNA viruses of plants," *PNAS USA*, Nov. 23, 1999, pp. 14147-14152, vol. 96, No. 24.

Wen, F.J. and Zhu, C.X. "Post-transcriptional gene silencing and virus resistance," *Chinese J. of Biotechnol*. May 2001, pp. 231-235, vol. 17, No. 3.

Zhang, et al., "Suppression of hepatitis B virus replication by microRNA-199a-3p and microRNA-210," *Antiviral Res.*, vol. 88: pp. 169-175, 2010.

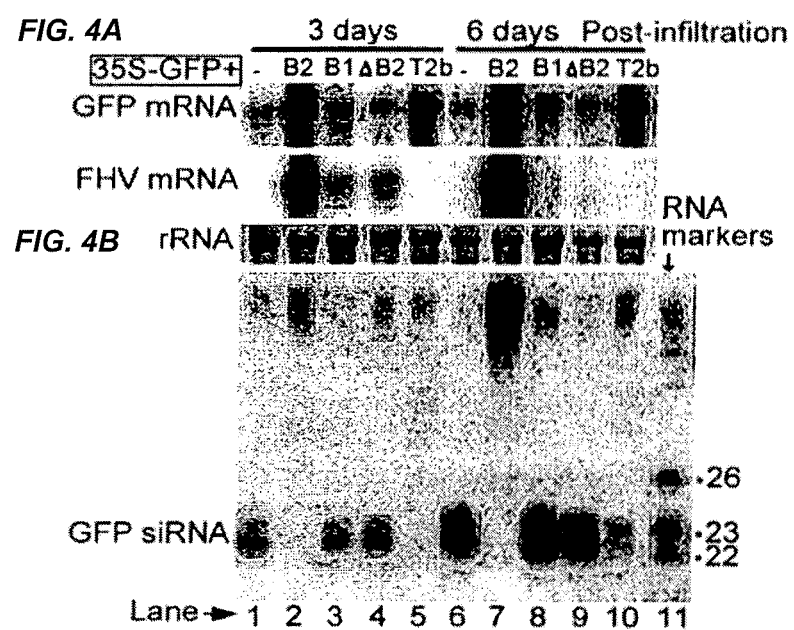

SEQUENCE LISTING

```
<160> NUMBER OF SEQ ID NOS: 2

<210> SEQ ID NO 1
<211> LENGTH: 160
<212> TYPE: PRT
<213> ORGANISM: Hepatitis C virus
<220> FEATURE:
<223> OTHER INFORMATION: F protein

<400> SEQUENCE: 1

Ala Arg Ile Leu Asn Leu Lys Lys Lys Thr Asn Val Thr Pro Thr Val
 1               5                  10                  15

Ala His Arg Thr Ser Ser Ser Arg Val Ala Val Arg Ser Leu Val Glu
             20                  25                  30

Phe Thr Cys Cys Arg Ala Gly Ala Leu Asp Trp Val Cys Ala Arg Arg
         35                  40                  45

Glu Arg Leu Pro Ser Gly Arg Asn Leu Glu Val Asp Val Ser Leu Ser
     50                  55                  60

Pro Arg Leu Val Gly Pro Arg Ala Gly Pro Gly Leu Ser Pro Gly Thr
 65                  70                  75                  80

Leu Gly Pro Ser Met Ala Met Arg Ala Ala Gly Arg Asp Gly Ser
             85                  90                  95

Cys Leu Pro Val Ala Leu Gly Leu Ala Gly Ala Pro Gln Thr Pro Gly
            100                 105                 110

Val Gly Arg Ala Ile Trp Val Arg Ser Ser Ile Pro Leu Arg Ala Ala
            115                 120                 125

Ser Pro Thr Ser Trp Gly Thr Tyr Arg Ser Ser Ala Pro Leu Leu Glu
        130                 135                 140

Ala Leu Pro Gly Pro Trp Arg Met Ala Ser Gly Phe Trp Lys Thr Ala
145                 150                 155                 160

<210> SEQ ID NO 2
<211> LENGTH: 540
<212> TYPE: RNA
<213> ORGANISM: Hepatitis C virus
<220> FEATURE:
<223> OTHER INFORMATION: F protein

<400> SEQUENCE: 2
augagcacga auccuaaacc ucaaaaaaaa aacaaacgua acaccaaccg ucgcccacag    60
gacgucaagu ucccgggugg cggucagauc guuguggag uuuacuuguu gccgcgcagg   120
ggcccuagau uggguguygcg cgcgacgaga aagacuuccg agcggucgca accucgaggu  180
```

```
                                    -continued agacgucagc cuaucccaa ggcucgucgg cccgagggca ggaccugggc ucagcccggg    240
uacccuuggc cccucuaugg caaugagggc ugcggguggg cgggauggcu ccugucuccc    300
cguggcucuc ggccuagcug gggcccaca gaccccggc guaggucgcg caauuugggu     360
aaggucaucg auacccuuac gugcggcuuc gccgaccuca ugggguacau accgcucguc   420 ggcgcccuc uuggaggcgc ugccagggcc cuggcgcaug gcguccgggu ucuggaagac    480
ggcgugaacu augcaacagg gaaccuuccu gguugcucuu ucucuaucuu ccuucuggcc   540
```

US 9,481,886 B2

RNA SILENCING IN ANIMALS AS AN ANTIVIRAL DEFENSE

CROSS-REFERENCES TO RELATED APPLICATIONS

The present patent application is a continuation of U.S. patent application Ser. No. 11/330,650, filed Jan. 11, 2006, which is a continuation of U.S. patent application Ser. No. 10/150,283, filed May 15, 2002, which is incorporated by reference herein in its entirety.

STATEMENT AS TO RIGHTS TO INVENTIONS MADE UNDER FEDERALLY SPONSORED RESEARCH AND DEVELOPMENT

This work was made with Government support under Grant No. 2002-35319-11537. awarded by the U.S. Department of Agriculture. The government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

RNA interference (RNAi) is a process where introduction of dsRNA into a cell causes destruction of RNA in a sequence-specific manner (see, D. Baulcombe, *Curr. Biol.*, 12:R83 (2002); Hutvagner et al., *Curr. Opin. Genet. Dev.*, 12:225 (2002)) RNAi has been observed in plants, *Neurospora*, flies, protozoans, and mice. Available data show that double-stranded (ds) RNA serves as the initial trigger of RNA interference and upon recognition, is processed by the Dicer RNAse into short fragments of 21 nucleotides (nt) in length. These short interfering (si)RNAs are then incorporated into a dsRNA-induced silencing complex (RISC) to guide cycles of specific RNA degradation.

Recent work has established that in higher plants targeted degradation of RNA occurs as a natural antiviral response, rather than simply being a response to artificially introduced or artificially induced dsRNA. Work by Dougherty and co-workers shows that virus infection is able to trigger RNA silencing of a homologous virus-derived transgene in transgenic tobacco (see, Lindbo et al., *Plant cell*, 5:1749-1759 (1993)). The activation of silencing is accompanied by recovery of the host from the initially virulent infection so that the new growth is both symptom and virus-free and is highly resistant to a secondary challenge by the same virus. This type of RNA-mediated virus resistance (RMVR), demonstrated conclusively for a number of dicot plant species with a variety of viruses (see, Waterhouse et al., *Trends Plant Sci.*, 4:452-457 (1999)), is also functional in monocot plants (see, Ingelbrecht et al., *Plant Physiol.*, 119:1187-1188 (1999)). This phenomenon, termed RNA silencing, has been shown to occur via a similar mechanism as RNA interference. Many plant RNA viruses have been found to encode efficient suppressors of RNA silencing. One such suppressor is the 2b protein encoded by cucumber mosaic cucumovirus (CMV). The idea that Cmv2b functions as a suppressor of host defense was first proposed based on the finding that Cmv2b is essential for the development of CMV disease symptoms in its hosts (see, Ding et al., *EMBO J*, 14:5762 (1995)). Previous analyses also indicated that the Cmv2b gene represents a newly evolved gene as compared to the other four CMV genes (see, Ding et al., *Virology*, 198:593-601 (1994)), suggesting that the Cmv2b gene is a viral adaptation to the RNA silencing antiviral defense in plants. Available evidence also shows that suppression of RNA silencing plays central role in the induction of viral disease in plants (see, Ding et al., *Curr. Opin. Biotechnol.*, 11(2): 152-156).

It is well established that cellular and humoral adaptive immunity based on peptide recognition are defenses employed against viruses by animals. However, little is known about other antiviral defenses in animals. In order to develop effective treatments for viral infections in mammals, it is necessary to identify and characterize these additional modes of antiviral defense. This invention fulfills these and other related needs.

BRIEF SUMMARY OF THE INVENTION

In one aspect, this invention provides recombinant DNA constructs for inactivation of a gene in a cell, where the constructs comprise polynucleotide sequence of a virus sufficient to activate RNA silencing and the polynucleotide sequence of the gene to be inactivated. In some embodiments, the sequence which activates RNA silencing is from the flock house virus (FHV). The constructs can either be infectious viral vectors or recombinant vectors. In certain embodiments, the constructs further comprise polynucleotide sequences enabling introduction into certain types of cells. In addition to inactivating genes in cells, the recombinant constructs of this invention can also be used to inactivate genes in a whole animal.

The gene inactivated by the recombinant constructs of this invention can be from a heterologous virus. Alternatively, the inactivated gene can be an endogenous gene. In certain embodiments, the endogenous gene is one where expression or overexpression of the endogenous gene induces a disease or a medical condition. The inactivated endogenous gene can be an oncogene.

In another aspect, the invention provides methods for identifying a RNA silencing suppressor. Typically, the methods comprise (a) introducing a polynucleotide sequence encoding FHV-ΔB2 into an animal cell; (b) introducing a polynucleotide sequence encoding a candidate RNA silencing suppressor into cell; and (c) testing for a rate or extent of FHV-ΔB2 RNA accumulation greater than that for a cell not contacted with the candidate suppressor. The method can be used to identify either silencing suppressors from a virus or an endogenous silencing suppressor.

In another aspect, the invention provides methods for identifying a viral RNA silencing suppressor by identifying a polynucleotide sequence that is an overlapping gene. In some embodiments, the gene overlaps with a RNA polymerase gene.

In yet another aspect, the invention provides methods for identifying an inhibitor of a RNA silencing suppressor. The methods typically comprise (a) infecting an animal cell with FHV; (b) contacting the cell with a candidate inhibitor of a RNA silencing suppressor; and (c) testing for a rate or extent of FHV RNA accumulation less than that for a cell not contacted with the candidate inhibitor. In certain embodiments, the candidate inhibitor is a small molecule. Typically, RNA accumulation is measured by visual assays for expressed reporter molecules and Northern blots.

In still yet another aspect, the invention provides methods for identifying a gene in the antiviral RNA silencing pathway of an animal. Typically, the methods comprise: (a) providing an animal cell expressing a polynucleotide encoding FHV-ΔB2; (b) inhibiting the expression of a candidate gene in the antiviral RNA silencing pathway; and (c) testing for a rate or extent of FHV-ΔB2 RNA accumulation greater than that for a cell where the expression of the candidate gene in the antiviral RNA silencing pathway has not been inhibited. In some embodiments, the polynucleotide encoding FHV-ΔB2 further comprises a reporter molecule, such as GFP. Typically, the expression of the candidate gene is inhibited by RNA interference, antisense DNA, or a ribozyme.

In still yet another aspect, this invention provides methods for identifying an enhancer of the antiviral RNA silencing pathway in an animal. The methods typically comprise (a) providing an animal cell infected with FHV; (b) contacting the cell with a candidate enhancer of the antiviral RNA silencing pathway; and (c) testing for a rate or extent of FHV RNA accumulation less than that for a cell which is not contacted with the candidate enhancer.

In another aspect, this invention provides methods for treating or preventing a viral infection in an animal. The methods typically comprise enhancing the antiviral RNA silencing pathway by contacting the animal with a compound that modulates a gene identified by the methods of this invention. In one embodiment, the gene is AGO2 or an AGO2 homologue.

DEFINITIONS

As defined herein, the term "inactivation" refers to the act of reducing or eliminating the expression of a particular gene.

The term "polynucleotide sequence of a virus sufficient to activate RNA silencing" or "polynucleotide sequence of a virus that activates RNA silencing", as used herein, refers to any portion of the viral genome which is capable of inducing degradation of viral or any other target RNA. Such polynucleotides typically lack sequences encoding functional viral RNA silencing suppressors. This is typically accomplished by deleting all or substantially all the sequences encoding suppressors or mutating suppressor sequences to disrupt or impair function. In certain instances, such polynucleotides can also encode natural suppressors with weak activity.

The term "polynucleotide sequence encoding FHV-ΔB2" or "polynucleotide encoding FHV-ΔB2", as used herein, refers to sequences that encode portions of the FHV genome sufficient to activate RNA silencing, but that do not encode a functional B2 protein (a viral RNA silencing suppressor). This is typically accomplished by deleting all or substantially all the sequence encoding B2, mutating the B2 sequence to disrupt function, or mutating the B2 sequence to reduce activity. "Polynucleotide sequences encoding FHV-ΔB2" can also encode other polypeptides, such as reporter molecules. In certain instances, these polynucleotides also comprise sequences which increase the host range of FHV or sequences which facilitate introduction of FHV into cells not normally susceptible to FHV infection.

As used herein, the term "recombinant vector" refers to a recombinant DNA construct which has polynucleotide sequences that enable either stable and heritable expression of the construct or transient expression in an host. Typically, such vectors are non-infectious and are introduced into cells via standard methods including, but not limited to calcium phosphate-mediated transfection, lipid-mediated transfection, electroporation, DNA guns, etc.

As used herein, the term "heterologous" refers to any sequence from another organism. For example, the term "polynucleotide sequences from heterologous viruses" as used herein refers to sequences from viruses other than the virus which provides the sequences that activate RNA silencing.

As used herein, the term "endogenous gene" refers to any gene which is a natural part of the genome and has not been introduced via artificial means.

The term "oncogene" refers to any gene which is capable of inducing neoplastic transformation. Oncogenes include, but are not limited to, src, fos, jun, myb, abl, etc.

The term "RNA silencing" as used herein refers to the degradation of RNA as a process induced by a natural "trigger", e.g., viral infection, rather than artificial manipulation, which is referred to as RNAi. In this application, the term specifically refers to the antiviral defense mechanism by which viral RNA is degraded in response to viral infection in a plant or animal cell.

The term "RNAi" or "RNA interference" as used herein refers to the degradation of RNA induced by introduction of dsRNA into a cell or manipulations designed to induce cells to produce artificial dsRNA.

The term "RNA silencing suppressor" as used herein refers to any polypeptide which is capable of blocking or reducing RNA silencing. RNA silencing suppressors in plants include p19 (tomato bushy stunt virus), CMV 2b (cucumomosaic virus), HC-Pro (potyviruses), P1 (rice yellow mottle sobemovirus), AC2 (African cassava mosaic geminovirus), and p25 (potato virus X). RNA silencing suppressors in animals include B2 (flock house virus).

The term "overlapping gene" as used herein refers to genes that share common nucleotide sequence but which encode distinct polypeptides due to different ORFs, stop points, or start points. "Overlapping genes" are primarily found in bacteria and viruses.

BRIEF DESCRIPTION OF THE DRAWINGS

FIG. 4A shows Northern blot analysis of total RNAs extracted 3 and 6 days after infiltration with 35S-GFP alone (−; lanes 1 & 6) or plus 35S-B2 (B2; lanes 2 & 7), 35S-B1 (B1; lanes 3 & 8), 35S-ΔB2 (ΔB2; lanes 4 & 9), or 35S-T2b (T2b; lanes 5 & 10). FIG. 4B shows the accumulation of GFP siRNAs.

DETAILED DESCRIPTION OF THE PREFERRED EMBODIMENTS

I. Overview

Figure 1:
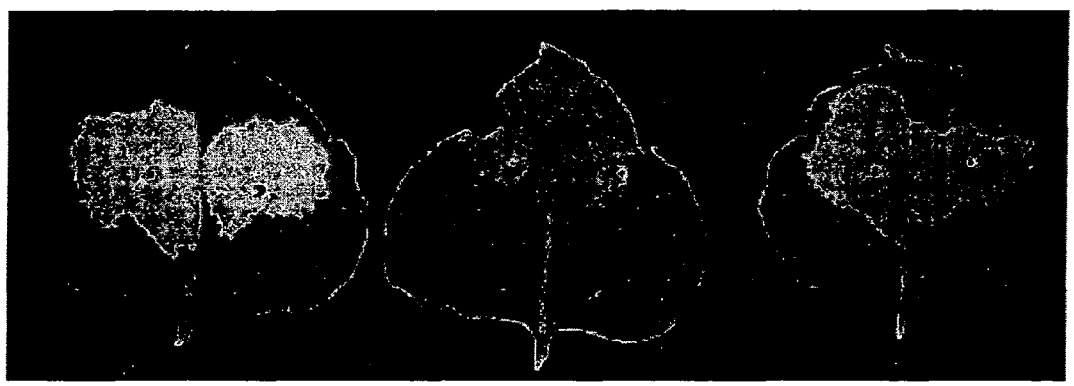
FIG. 1 illustrates cross-kingdom suppression of RNA silencing in plants by an animal viral protein. The GFP-expressing *Nicotiana benthamiana* leaves were co-infiltrated with a mixture of two *Agrobacterium tumefaciens* strains as described (Voinnet et al., *Cell*, 103:157 (2000); Guo et al., *EMBO J*, 21:398 (2002)). One directs expression of GFP and thereby induces GFP RNA silencing and the other simultaneously expresses B2 (left leaf), 2b (right leaf) or an untranslatable 2b coding sequence (middle leaf). The leaves were detached and photographed under UV illumination 6 days post-infiltration. GFP silencing is visualized in the control leaf (middle) as a bright red color zone surrounding the infiltrated patch due to chlorophyll fluorescence.

This invention is based on the discovery that RNA silencing acts as an antiviral defense mechanism in animal cells. Specifically, this invention establishes that a virus can induce strong viral RNA silencing and that the same viruses are equipped with an effective silencing suppressor essential for infection. Prior to this discovery, it was known that RNA degradation could be artificially induced by dsRNA in animals and that RNA silencing was an antiviral defense mechanism in plants, but it was not known that RNA degradation could occur in response to a natural trigger, i.e, a virus, in animals.

The discovery of a novel animal antiviral defense mechanism offers immense opportunities for treating human and animal viral diseases and for gene therapy. For example, viral infections can be treated by enhancing the RNA silencing antiviral defense response, or by blocking the action of suppressors of RNA silencing. In addition, since RNA viruses are potent initiators of RNA silencing, foreign sequences from endogenous human genes or heterologous viruses can be inserted into attenuated RNA viruses to produce a novel class of therapeutic vectors for either inactivating certain human genes (gene therapy) or targeting other viruses in trans (as a live attenuated vaccine).

In one aspect, this invention provides recombinant DNA constructs comprising viral sequence sufficient to activate RNA silencing. Such polynucleotides typically lack sequences encoding functional viral RNA silencing suppressors. In another aspect, the invention provides methods of identifying additional RNA silencing suppressors. Suppressors can be identified by functional methods using recombinant DNA constructs of this invention or by bioinformatic/sequence analysis methods to identify other genes with similar key features. In another aspect, this invention provides recombinant DNA constructs for inactivating genes, wherein the construct comprises viral sequence sufficient to activate RNA silencing and a target gene for inactivation. In still yet another aspect, this invention provides methods for identifying genes in the antiviral RNA silencing pathway using recombinant DNA constructs of this invention. This invention also provides methods for identifying modulators of the RNA silencing suppressors and the antiviral RNA silencing pathway, as well as methods for treating animals infected with virus and for preventing viral infections by upregulating the antiviral pathway.

Preparation of recombinant DNA constructs for activation of RNA silencing is described in detail in Section II of this application. Embodiments of the invention which use these constructs are described in Sections III to VIII.

II. Vectors that Activate RNA Silencing

This invention provides vectors with viral polynucleotide sequences sufficient to activate RNA silencing. These vectors have multiple uses, including identification of RNA silencing suppressors (Section III), gene therapy (Section N), and identification of genes in the antiviral RNA silencing defense pathway (Section V).

These vectors typically lack sequences encoding functional viral RNA silencing suppressors. This is typically accomplished by deleting all or substantially all the sequences encoding suppressors, mutating suppressor sequences to disrupt function, or mutating suppressor sequences to reduce activity. In certain instances, the polynucleotides can also encode natural suppressors with weak activity.

One of skill will recognize that the viral polynucleotide sequence can be from any virus capable of inducing RNA silencing. In one embodiment, the vector used for gene inactivation comprises polynucleotide portions of FHV sufficient to activate RNA silencing.

In certain embodiments, the vectors are infectious viral vectors. Such vectors comprise a viral genome and the target gene. Typically, the viral genome has been modified to remove sequences that confer virulence.

Infectious viral vectors of this invention are typically capable of infecting a broad range of hosts including humans, dogs, cats, horses, cows, monkey, etc.; usually, these viral vectors are capable of efficiently infecting all humans. Any viruses that have been developed for use as gene therapy vectors can be used. Exemplary viruses include retroviruses (including lentiviruses), adenoviruses, adeno-associated viruses, herpes simplex virus type 1, etc. Additionally, viral vectors can be derived from the genome of human or bovine adenoviruses, vaccinia virus, herpes virus, minute virus of mice (MVM), HIV, sindbis virus, Rous sarcoma virus, and MoMLV. In certain embodiments, the infectious viral vectors of this invention further comprise polynucleotide sequences that alter the host range. Infectious viral vectors with a host range different from or broader than that of the native viral polynucleotide sequence can be constructed by incorporating these determinants of host range.

In another embodiment, the invention provides non-infectious recombinant vectors (amplicons) which can be introduced into a cell to produce a stable and heritable phenotype. For example, an amplicon can comprise a promoter and terminator which directs transcription of modified viral vector RNA. The modifications can include deletion or mutation of viral genes required for spread of the virus or any other functions that are secondary to replication.

In certain embodiments, these vectors can have inverted repeats in the transcribed regions. In yet another embodiment, the invention provides non-infectious transgenic vectors that are only transiently expressed in the host cell.

Non-infectious vectors can be introduced into cells using standard methods known to those of skill in the art. Such methods include electroporation, the use of DNA guns, calcium-phosphate mediated transfection, lipid-mediated transfection, the use of kits designed for such purposes, and the like. The vectors can also be introduced via other systems including, but not limited, to an HVJ (Sendai virus)-liposome gene delivery system (see, e.g., Kaneda et al., *Ann. N.Y. Acad. Sci.* 811:299-308 (1997)); a "peptide vector" (see, e.g., Vidal et al., *CR Acad. Sci III* 32:279-287 (1997)); as a gene in an episomal or plasmid vector (see, e.g., Cooper et al., *Proc. Natl. Acad. Sci. U.S.A.* 94:6450-6455 (1997), Yew et al. *Hum Gene Ther.* 8:575-584 (1997)); as a gene in a peptide-DNA aggregate (see, e.g., Niidome et al., *J. Biol. Chem.* 272:15307-15312 (1997)); as "naked DNA" (see, e.g., U.S. Pat. No. 5,580,859 and U.S. Pat. No. 5,589,466); in lipidic vector systems (see, e.g., Lee et al., *Crit Rev Ther* Drug Carrier Syst. 14:173-206 (1997)); polymer coated liposomes (Marin et al., U.S. Pat. No. 5,213,804, issued May 25, 1993; Woodle et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994;

Portions of a virus sufficient to activate RNA silencing can easily be identified using standard mutagenesis and deletion methods known to those of skill in the art. For example, a vector comprising a viral genome with various deletions and lacking functional RNA silencing suppressors, can be transfected into cells and tested for RNA silencing activity. Assays for RNA silencing include measuring accumulation of viral RNA or detecting intermediates produced during RNA degradation, e.g., siRNA, etc. Methods for detecting and quantifying RNA are described in Section VI, Part B, below.

Vectors of the present invention can be constructed using standard methods in molecular biology, such as those described in many general molecular biology textbooks such as Sambrook et al., Molecular Cloning a Laboratory Manual 2nd Ed. Cold Spring Harbor Press, Cold Spring Harbor (1989) and Ausubel et al., Current Protocols in Molecular Biology, (current edition).

III. Identification of RNA Silencing Suppressors

In one aspect, this invention provides RNA silencing suppressors of animal viruses. These animal viruses can be DNA or RNA viruses. A particular virus may encode more than one RNA silencing suppressor.

In one embodiment, the invention provides a RNA silencing suppressor for FHV called B2. In other embodiments, this invention provides RNA silencing suppressors for other animal viruses, including those viruses where infection is widespread, has severe effects, or where there has been limited success in developing effective vaccines or therapeutics. Exemplary viruses include HIV, HCV, HBV, influenza viruses, measles virus etc. In certain embodiments, the present invention also provides methods of identifying endogenous/cellular RNA silencing suppressors (see, Anandalakshmi et al., *Science,* 290:142-144 (2000)).

Silencing suppressors can be identified using the teachings provided here and standard methods known to those of skill in the art. For example, suppressors are identified by sequence analysis, functional tests using vectors described in Section II, or combinations herewith.

A. Sequence Analysis

A majority of known plant viral RNA silencing suppressors are "overlapping" genes (see, Table 1).

TABLE I

| Virus name | Genome type | Suppressor gene | Overlapped gene | Reference |
|---|---|---|---|---|
| Cucumber mosaic virus | Plus-strand RNA | 2b | RNA-dependent RNA polymerase (RdRP) | Brigneti et al. *EMBO J* 17: 6739-6746 (1998) |
| Tomato aspermy virus | Plus-strand RNA | 2b | RdRP | Li et al. *EMBO J* 18: 2683-2691 (1999) |
| Tomato bushy stunt virus | Plus-strand RNA | p19 | Movement protein (p23) | Voinnet et al. PNAS USA 96: 14147-14152 (1999) |
| Africa cassava mosaic virus | Single-stranded circular DNA | AC2 | Replication-associated protein (AC1) | Voinnet et al. PNAS USA 96: 14147-14152 (1999) |
| Turnip yellow mosaic virus | Plus-strand RNA | OP | RdRP | Ding S W, unpublished data |
| Potato virus X | RNA | p25 | p12 | |

For example, the RNA silencing suppressor for the cucumber mosaic virus is an overlapping gene in the +1 frame of the viral RNA-dependent RNA polymerase (RdRP) gene. Similarly, the viral RNA silencing suppressor for FHV is also an overlapping gene in the +1 frame of the viral RNA polymerase gene.

Thus analysis of viral genomes can be used to identify RNA silencing suppressors. Viral genomes are thus conveniently examined for "overlapping" genes. Overlapping genes are often conserved only in a specific taxonomic grouping and their encoded proteins are likely to have unusual biochemical properties. In some embodiments, particular attention is paid to "overlapping" genes of RNA polymerase in the +1 reading frame. However, it will be readily appreciated by those of skill in the art that putative viral RNA silencing suppressors are not limited to this particular embodiment; the suppressors can overlap with any gene in any reading frame.

In some embodiments, viral genomes will be examined for genes that appear to be required for virulence and virus accumulation, but for which there is no known specific function. Viral genomes are also typically examined for genes that are essential for viral infection in certain cell types but not essential in other cell types. Genes with these characteristics are good candidates for suppressor genes.

As an example, the gene F has been identified as a RNA silencing suppressor for HCV based on sequence analysis. The F protein is a novel protein synthesized from the initiation codon of the HCV polyprotein followed by a ribosomal frameshift into the −2/+1 reading frame (see, SEQ ID NO:1-2; Xu et al. *EMBO J* 20:3840 (2001)). Table 2 lists other RNA silencing suppressors for various viruses.

TABLE 2

| Virus name | Genome type | Suppressor | Overlapped gene | Reference |
|---|---|---|---|---|
| HIV-1 and HIV-2 | RNA | tat, rev | env | Keese & Gibbs PNAS 89: 9489-9493 (1992) |
| HIV-1 | RNA | vpu | env | Keese & Gibbs PNAS 89: 9489-9493 (1992) |

TABLE 2-continued

| Virus name | Genome type | Suppressor | Overlapped gene | Reference |
|---|---|---|---|---|
| HIV-2 | RNA | vpx | vif | Keese & Gibbs PNAS 89: 9489-9493 (1992) |
| Measles virus | RNA | C and V | P | Fields Virology, Fourth Edition. 2001 Chpt 44 |
| Influenza virus B | RNA | NB | NA | Fields Virology, Fourth Edition. 2001 Chpt 46 |
| Influenza virus B | RNA | BM2 | M1 | Fields Virology, Fourth Edition. 2001 Chpt 46 |
| Influenza virus A/B/C | RNA | NS1/NS2 | NS1/NS2 | Fields Virology, Fourth Edition. 2001 Chpt 46 |
| Papillomaviruses | DNA | E4 | E2 | Fields Virology, Fourth Edition. 2001 Chpt 65 |
| Hepadnaviruses (includes Hepatitis B virus) | DNA | X | P | Fields Virology, Fourth Edition. 2001 Chpt 86 |
| Hepatitis C virus | RNA | F | C | Xu et al. *EMBO J* 20: 3840 (2001) |

Once putative RNA silencing suppressors are identified, they can be tested using any functional test known to those of skill in the art, such as those described in the following section.

B. Functional Analysis

RNA silencing suppressors can also be identified via functional tests using vectors described in Section II. Typically, a test will examine the ability of a polypeptide encoded by a candidate RNA silencing suppressor gene to hinder, block, or slow RNA silencing induced by the viral vector. RNA levels in a cell can be measured using methods described in Section VI, Part B, below.

In certain embodiments, the method comprises expressing a polynucleotide sequence of a virus sufficient to activate RNA silencing as defined herein ("silenced viral sequence") in a cell, introducing a polynucleotide encoding a candidate RNA silencing suppressor into the cell, and testing for increased rate or extent of accumulation of the "silenced viral sequence".

It will be appreciated that the polynucleotide sequence can be part of either an infectious vector or a non-infectious vector. It will further be appreciated that the "silenced viral sequence" and candidate suppressor sequence can either be on the same or different vector and introduced at varying times. In some embodiments, the "silenced viral sequence" is introduced before the candidate suppressor gene. Based on studies with plant suppressors, it is known that certain viral RNA silencing suppressors target early stages of RNA silencing, while others target later stages (see, Li and Ding. Viral suppressors of RNA silencing. *Curr. Opin. Biotech.,* 12:150-154 (2001). Suppressors which target early stages of the RNA silencing pathway are unlikely to be active unless expressed before or during the initiation of RNA silencing. Therefore, in some embodiments, the suppressor gene is either introduced before or during RNA silencing—either on the same vector as the "silenced viral sequence", on a separate vector prior to introduction of the "silenced viral sequence", or on the same vector as the "silenced viral sequence" but engineered to be expressed first.

The "silenced viral sequence" can be expressed in any animal cell where the antiviral RNA silencing pathway is activated in response to the "silenced viral sequence". In certain embodiments, *Drosophila* cells are used.

Candidate RNA silencing suppressors can be any gene identified by sequence analysis described in the above section or any other gene which has properties or a sequence which suggest that the gene may be a RNA silencing suppressor. For identification of viral RNA silencing suppressors, the candidate gene can be from a virus. For identification of endogenous suppressors, the candidate gene can be from the genome of the same organism as the host cell, or from the genome of a different organism.

RNA accumulation of the "silenced viral sequence" can be measured using any method known to those of skill in the art, such as those described in Section VI, Part B; these methods include Northern blot or assays to detect reporter molecules linked to the polynucleotide. The reporter molecules can either be detectable fluorescence molecules or selectable antibiotic markers. In one embodiment, RNA accumulation is detected using an where the first polynucleotide is coupled to GFP. Suppression of RNA silencing allows expression of GFP, which can be visualized by UV illumination. Active RNA silencing generates a red fluorescent zone.

In one embodiment, the "silenced viral sequence" encodes FHV-ΔB2. It has been demonstrated that a vector encoding such a sequence is deficient in silencing suppression and does not accumulate to detectable levels in *Drosophila* cells; however, this defect can be rescued in trans by co-transfection with a plasmid expressing B2.

IV. Gene Therapy & Vaccination Against Pathogens

In certain embodiments, the above-described vectors for inducing RNA silencing (Section II) further comprise a target gene, wherein inactivation of the target gene is desired. Those of skill in the art will recognize that vectors of this invention can be used for any application where a reduction in mRNA expression levels of specific genes or the protein expression levels of specific genes is desired. The vectors of this invention are particularly useful for methods where targeted inactivation of closely related multigene families is desired. Any gene that can be targeted with antisense technology can also be targeted with this invention.

In certain embodiments, the target genes for the vectors of this invention are portions of heterologous pathogen genomes wherein inactivation of such portions is sufficient to reduce or eliminate infection by the pathogen. In a typical embodiment, the pathogen will be a virus. By activating sustained RNA degradation of these viral genomes, these vectors are expected to be useful for both the treatment and prevention of viral infections in animals.

In other embodiments, the target genes for the vectors are endogenous genes. Typically, the endogenous genes are ones where the expression or overexpression of such genes induces a disease or a medical condition. In some embodiments, the targeted endogenous genes encode polypeptides that contribute to cancer, such as oncogenes, e.g., src, abl, ras, etc. and growth factors, such as the epidermal growth factor. In other embodiments, the targeted endogenous gene encodes a polypeptide that promotes abnormal angiogenesis, a factor that contributes to tumor growth and ocular diseases (e.g., diabetic retinopathy and macular degeneration). Such angiogenesis-promoting polypeptides include vascular endothelial growth factor (VEGF). In still other embodiments, the vectors can be used to treat any monogenic autosomal dominant disease (e.g., familial hypercholesteremia, dominant forms of retinal degeneration, Huntington's disease, myotonic dystrophy, hemophilia, etc.). In contrast to autosomal recessive diseases, treatment of these diseases requires that an aberrant gene is silenced (see, Gerard and Collen, Cardiovascular Research 35:451-458 (2001)).

In other embodiments, the endogenous genes are ones where it is desirable to understand the precise function of the genes or the effect of inactivating the gene. Such vectors are valuable tools in functional genomic screening assays.

In still other embodiments, the endogenous genes are ones where inactivation the genes can be used to generate animal models for disease. Typically, these diseases are monogenic diseases where deletion of a single gene or mutation to generate a nonfunctional gene is sufficient to induce a disease phenotype (i.e., monogenic disease), such as cystic fibrosis, Duchenne muscular dystrophy, hemophilia, ADA deficiency, and familial hypercholesteremia. For example, a vector which activates silencing of the CFTR genes can be used to generate an animal model for cystic fibrosis.

V. Methods for Identifying Genes in the Antiviral RNA Silencing Pathway

This invention further provides methods for identifying genes in the antiviral RNA silencing pathway using vectors described in Section H. By identifying viral RNA silencing suppressors, this invention provides vectors which can be used as tools to determine whether a particular gene is part of the antiviral defense pathway. These "reporter vectors" can be any vector expressing viral polynucleotide sequences sufficient to activate RNA silencing as defined herein, i.e., any vector which is rapidly degraded after expression. Genes in the antiviral silencing pathway are identified by inhibiting the expression of a candidate gene in cells expressing the "reporter vector" and looking for an increased rate or extent of viral RNA accumulation.

In some embodiments, the "reporter vector" comprises portions of the FHV genome sufficient to activate RNA silencing, lacking a functional RNA silencing suppressor, and linked to a reporter molecule. The vector can also comprise additional polynucleotide sequences which increase the host range of FHV or sequences which facilitate introduction of the vector into cells. In one embodiment, the "reporter vector" encodes FHV-ΔB2 linked to a reporter molecule, such as GFP.

The above-described "reporter vectors" can be engineered to be expressed in any animal cell where it is capable of activating an antiviral RNA silencing pathway. The "reporter vector" can be used to identify components of the antiviral pathway for the particular type of animal that the cell is derived from. For example, introduction of the "reporter vector" into a Drosophila cell will allow identification of fly antiviral RNA silencing pathway genes. Sequence analysis can be used to identify homologues in other organisms.

Expression of a candidate gene in the antiviral defense pathway can be inhibited using any standard method known to those of skill in the art, such as RNA interference, antisense molecules and ribozymes. Accumulation of the above-described "reporter vectors" can be measured using standard methods for detection of RNA. In certain embodiments, the vectors are coupled to a tag or label which allows visual detection of the expression product, such as GFP.

This invention further comprises any novel genes identified by such a method.

VI. Methods for Identifying Modulators of RNA Silencing Suppressors and Modulators of Genes in the Antiviral RNA Silencing Pathway In certain embodiments, the invention comprises methods for identifying modulators of RNA silencing suppressors and modulators of the antiviral RNA silencing pathway. Typically, the methods of this invention are used to identify inhibitors of RNA silencing suppressors and enhancers of the antiviral RNA silencing pathway. The term "test compound" or "drug candidate" or "modulator" or grammatical equivalents as used herein describe any molecule, e.g., protein, oligopeptide, small organic molecule, polysaccharide, polynucleotide, etc., to be tested for the capacity to directly or indirectly alter the activity of RNA silencing suppressors and/or genes in the antiviral RNA silencing pathway.

In some embodiments, an animal cell or animal is infected with virus and the animal cell is contacted with a candidate modulator or the animal is "administered" the modulator. By "administration" or "contacting" herein is meant that the candidate agent is administered in such a manner as to allow the agent to act upon the animal. Generally, a plurality of different modulator concentrations are tested to obtain a differential response to the various concentrations. Typically, one of these concentrations serves as a negative control, i.e., at zero concentration or below the level of detection.

A. Compounds & Biomolecules to be Screened

The compounds tested as modulators of the activity of RNA silencing suppressors and the antiviral RNA silencing pathway can be any small chemical compound, or a biological entity, such as a protein, sugar, nucleic acid or lipid. Alternatively, modulators can be genetically altered versions of the genes. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

1. Combinatorial Chemistry Libraries

In certain embodiments, combinatorial libraries of potential modulators will be screened for an ability to bind to modulate RNA silencing suppressors and components of the antiviral RNA silencing defense pathway. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds.

In one embodiment, the drug screening method involves providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature,* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA,* 90:6909-6913 (1993)), vinylogous polypeptides (Hagihara et al., *J. Amer. Chem. Soc.,* 114:6568 (1992)), nonpeptidal peptidomimetics with glucose scaffolding (Hirschmann et al., *J. Amer. Chem. Soc.,* 114:9217-9218 (1992)), analogous organic syntheses of small compound libraries (Chen et al., *J. Amer. Chem. Soc.,* 116:2661 (1994)), oligocarbamates (Cho et al., *Science,* 261:1303 (1993)), and/or peptidyl phosphonates (Campbell et al., *J. Org. Chem.,* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. The above devices, with appropriate modification, are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

2. Proteins and Nucleic Acids as Potential Modulators

In one embodiment, the modulators are proteins, often naturally occurring proteins Or fragments of naturally occurring proteins. Thus, e.g., cellular extracts containing proteins, or random or directed digests of proteinaceous cellular extracts, may be used. In this way libraries of proteins may be made for screening in the methods of the invention. These can include, but are not limited to, libraries of bacterial, fungal, viral; and mammalian proteins. Typically, the libraries comprise human proteins.

In one embodiment, modulators are peptides of from about 5 to about 30 amino acids, from about 5 to about 20 amino acids, or from about 7 to about 15. The peptides may be digests of naturally occurring proteins as is outlined above, random peptides, or "biased" random peptides. By "randomized" or grammatical equivalents herein is meant that the nucleic acid or peptide consists of essentially random sequences of nucleotides and amino acids, respectively. Since these random peptides (or nucleic acids, discussed below) are often chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. Typically, the library is biased. That is, some positions within the sequence are either held constant, or are selected from a limited number of possibilities. In another embodiment, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc.

Modulators can also be nucleic acids, as defined above. As described above generally for proteins, nucleic acid modulating agents may be naturally occurring nucleic acids, random nucleic acids, or "biased" random nucleic acids. Digests of prokaryotic or eukaryotic genomes may be used as is outlined above for proteins.

B. The Screening Process

Candidate modulators can be identified by infecting animal cells with any native virus which activates RNA silencing. The effect of such modulators can then be determined by measuring accumulation of viral RNA. RNA levels can be determined using any standard method known to those of skill in the art, such as visual assays indicating transcription of reporter molecules or Northern blots. In other embodiments, RNA levels can be measured using labeled probes or amplification-based assays.

Probes to detect RNA can be a nucleotide/deoxynucleotide probe that is complementary to and hybridizes with the RNA and includes, but is not limited to, oligonucleotides, cDNA or RNA. Probes also should contain a detectable label as defined in the art. In one method the RNA is detected after immobilizing the RNA to be examined on a solid support such as nylon membranes and hybridizing the probe with the sample. Following washing to remove the non-specifically bound probe, the label is detected. In another method detection of the RNA is performed in situ. In this method permeabilized cells or tissue samples are contacted with a detectably labeled nucleic acid probe for sufficient time to allow the probe to hybridize with the target RNA. Following washing to remove the non-specifically bound probe, the label is detected. For example a digoxygenin labeled riboprobe (RNA probe) that is complementary to the RNA is detected by binding the digoxygenin with an anti-digoxygenin secondary antibody and developed with nitro blue tetrazolium and 5-bromo-4-chloro-3-indoyl phosphate.

Often, amplification-based assays are performed to measure the expression level of viral RNAs. These assays are typically performed in conjunction with reverse transcription. In such assays, a nucleic acid sequence acts as a template in an amplification reaction (e.g., Polymerase Chain Reaction, or PCR). In a quantitative amplification, the amount of amplification product will be proportional to the amount of template in the original sample. Comparison to appropriate controls provides a measure of the amount of RNA. Methods of quantitative amplification are well known to those of skill in the art. Detailed protocols for quantitative PCR are provided, e.g., in Innis et al., PCR Protocols, A Guide to Methods and Applications (1990).

In some embodiments, a TaqMan based assay is used to measure expression. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, e.g., literature provided by Perkin-Elmer, e.g., www2.perkinelmer.com).

Other suitable amplification methods include, but are not limited to, ligase chain reaction (LCR) (see Wu & Wallace, *Genomics*, 4:560 (1989), Landegren et al., *Science*, 241: 1077 (1988), and Barringer et al., *Gene*, 89:117 (1990)), transcription amplification (Kwoh et al., *Proc. Natl. Acad. Sci. USA*, 86:1173 (1989)), self-sustained sequence replication (Guatelli et al., *Proc. Nat. Acad. Sci. USA*, 87:1874 (1990)), dot PCR, and linker adapter PCR, etc.

VII. Therapeutic and Prophylactic Applications

This invention also provides methods for treating or preventing viral infection by upregulating degradation of viral RNA and thus reducing virus levels. Typically, degradation of viral RNA is upregulated by either activating the antiviral RNA silencing pathway or inhibiting any RNA silencing suppressors using modulators identified with methods of this invention.

In one embodiment, the antiviral silencing pathway is activated by administering a pharmaceutical composition that either upregulates the expression level of a gene in the pathway or enhances of the activity of a gene in the pathway. The gene can be one identified by the methods of this invention. In one embodiment, the activity or expression level of AGO2 or an AGO2 homologue is increased.

In another embodiment, the suppression of RNA silencing is blocked or reduced by administering a pharmaceutical composition that either inhibits the activity of a RNA silencing suppressor or reduces the expression level of a RNA silencing suppressor. Compounds with these particular attributes can be identified using methods of this invention. Pharmaceutical compositions, dosages, and administration modes are described below.

VIII. Compositions Comprising Modulators Identified in this Invention or Gene Therapy Vectors & Pharmaceutical Administration of Such Compositions A. Dosage In one embodiment, a therapeutically effective dose of a gene therapy vector or a modulator of a RNA silencing suppressor or gene in the antiviral RNA silencing pathway is administered to a patient. By "therapeutically effective dose" herein is meant a dose that produces effects for which it is administered. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). As is known in the art, adjustments for systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus the methods are applicable to both human therapy and veterinary applications. Typically, the patient is a mammal and usually the patient is human.

B. Administration & Pharmaceutical Compositions

The administration of the gene therapy vectors or modulators of the present invention can be done in a variety of ways as discussed above, including, but not limited to, orally, subcutaneously, intravenously, intranasally, transdermally, intraperitoneally, intramuscularly, intrapulmonary, vaginally, rectally, intraocularly, or directly applied as a solution or spray.

The pharmaceutical compositions of the present invention comprise modulators in a form suitable for administration to a patient. In one embodiment, the pharmaceutical compositions are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that protein modulators (e.g., antibodies, gene therapy constructs, ribozymes, small organic molecules, etc.) when administered orally, should be protected from digestion. It is also recognized that, after delivery to other sites in the body (e.g., circulatory system, lymphatic system, or the tumor site) the modulators of the invention may need to be protected from excretion, hydrolysis, proteolytic digestion or modification, or detoxification by the liver. In all these cases, protection is typically accomplished either by complexing the molecule(s) with a composition to render it resistant to acidic and enzymatic hydrolysis, or by packaging the molecule(s) in an appropriately resistant carrier, such as a liposome or a protection barrier or by modifying the molecular size, weight, and/or charge of the modulator. Means of protecting agents from digestion degradation, and excretion are well known in the art.

The compositions for administration will commonly comprise a gene therapy vector or modulator dissolved in a pharmaceutically acceptable carrier, typically, an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacologial Basis of Therapeutics (Hardman et al., eds., 1996)).

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., Remington's Pharmaceutical Science and Goodman and Gillman, The Pharmacologial Basis of Therapeutics, supra.

The compositions containing gene therapy vectors or modulators can be administered for therapeutic or prophylactic treatments to treat the disease or conditions being treated, such as a viral infection. In therapeutic applications, compositions are administered to a patient suffering from a disease in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of a disease in a mammal is referred to as a "prophylactically effective dose." The particular dose required for a prophylactic treatment will depend upon the medical condition and history of the mammal, the particular disease being prevented, as well as other factors such as age, weight, gender, administration route, efficiency, etc. Such prophylactic treatments may be used, e.g., in a mammal who has previously had a disease to prevent a recurrence of the disease, or in a mammal who is expected to be susceptible to such a disease.

It will be appreciated that the present modulating compounds can be administered alone or in combination with additional modulating compounds or with other therapeutic agent for treatment of the particular disease or condition, e.g., for treatment of viral infection, the composition can be administered together with other agents or treatments that enhance the immune response to viral infection.

C. Issues Specific to Administration and Formulation of Gene Therapy Constructs

In some embodiments of the invention, gene therapy constructs are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, gene constructs can be linked through a polylysine moiety to asialo-oromucocid, which is a ligand for the asialoglycoprotein receptor of hepatocytes.

Similarly, viral envelopes used for packaging gene constructs can be modified by the addition of receptor ligands or antibodies specific for a receptor to permit receptor-mediated endocytosis into specific cells (see, e.g., WO 93/20221, WO 93/14188, WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88: 8850-8854 (1991)). In other embodiments, molecular conjugates of the instant invention can include microtubule inhibitors (WO/9406922); synthetic peptides mimicking influenza virus hemagglutinin (Plank et al., *J. Biol. Chem.* 269:12918-12924 (1994)); and nuclear localization signals such as SV40 T antigen (WO93/19768).

When used for pharmaceutical purposes, the formulations of the invention include a buffer that can contain a delivery-enhancing compound. The buffer can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. (1966) *Biochemistry* 5:467. The pH of the buffer in the pharmaceutical composition comprising a gene therapy construct, for example, is typically in the range of 6.4 to 8.4, 7 to 7.5, or 7.2 to 7.4.

The compositions of this invention can additionally include a stabilizer, enhancer or other pharmaceutically acceptable carriers or vehicles. A pharmaceutically acceptable carrier can contain a physiologically acceptable compound that acts, for example, to stabilize the gene therapy construct. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier depends on the route of administration and the particular physio-chemical characteristics of the gene therapy vector. Examples of carriers, stabilizers or adjuvants can be found in Martin, *Remington's Pharm. Sci.*, 15th Ed. (Mack Publ. Co., Easton, Pa. 1975), which is incorporated herein by reference.

The gene therapy vector can be delivered to any tissue or organ, including neoplastic tissues such as cancer tissue, using any delivery method known to the ordinarily skilled artisan for example, intratumoral or intravesical administration. Tissues and organs include any tissue or organ having an epithelial membrane such as the gastrointestinal tract, the bladder, respiratory tract, and the lung. Examples include but are not limited to carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, colon and rectum, gallbladder, or skin; or melanoma.

In some embodiments of the invention, the therapeutic agent is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701. Such formulations are especially useful for the treatment of cancers of the mouth, head and neck cancers (e.g., cancers of the tracheobronchial epithelium) skin cancers (e.g., melanoma, basal and squamous cell carcinomas), cancers of the intestinal mucosa, vaginal mucosa, and cervical cancer.

The formulations of the invention are typically administered to enhance transfer of an agent to a cell. The cell can be provided as part of a tissue, such as an epithelial membrane, or as an isolated cell, such as in tissue culture. The cell can be provided in vivo, ex vivo, or in vitro. In some embodiments of the invention, the compositions of the invention are administered ex vivo to cells or tissues explanted from a patient, then returned to the patient. Examples of ex vivo administration of therapeutic gene constructs include Arteaga et al., *Cancer Research* 56(5): 1098-1103 (1996); Nolta et al., *Proc Natl. Acad. Sci. USA* 93(6):2414-9 (1996); Koc et al., *Seminars in Oncology* 23 (1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

EXAMPLES

The following examples are offered to illustrate, but not to limit the claimed invention.

Example 1

This example illustrates that RNA silencing is a natural antiviral defense mechanism in animals and that certain animal viruses encode RNA silencing suppressors to counter this defense mechanism.

Summary

RNA silencing is a sequence-specific RNA degradation mechanism that is operational in plants and animals. Here we show that flock house virus (FHV) is both an initiator and a target of RNA silencing in *Drosophila* host cells and that FHV infection requires suppression of RNA silencing by a FHV-encoded protein, B2. These findings establish RNA silencing as a novel adaptive antiviral defense in animal cells. B2 also inhibits RNA silencing in transgenic plants, providing evidence for a conserved RNA silencing pathway in the plant and animal kingdoms.

Background

Posttranscriptional gene silencing, quelling and RNA interference (RNAi) are mechanistically related RNA silencing processes that destroy RNA in a sequence-specific manner (D. Baulcombe, *Curr. Biol.*, 12:R83 (2002); Hutvagner et al., *Curr. Opin. Genet. Dev.*, 12:225 (2002)).

Available data show that double-stranded (ds) RNA serves as the initial trigger of RNA silencing and upon recognition, is processed by the Dicer RNase into short fragments of 21 nucleotides (nt) in length. These short interfering (si)RNAs are then incorporated into a dsRNA-induced silencing complex (RISC) to guide cycles of specific RNA degradation (D. Baulcombe, *Curr. Biol.*, 12:R83 (2002); Hutvagner et al., *Curr. Opin. Genet. Dev.*, 12:225 (2002)). Here we report that RNA silencing plays a natural antiviral role in animal cells as has been established in plants (Vance et al., *Science*, 292:2277 (2001); Li et al., *Curr. Opin. Biotechnol.*, 12:150 (2001)).

The B2 gene of FHV shares key features, but not sequence similarity, with the plant cucumoviral 2b gene (Ding et al., *EMBO J*, 14:5762 (1995)), which encodes a known group of silencing suppressors (Brigneti et al., *EMBO J*, 17:6739 (1998); Li et al., *EMBO J*, 18:2683 (1999)). Both open reading frame (ORF) 2b and B2 overlap the carboxyl terminal region and occupy the +1 reading frame of the ORF encoding the viral RNA-dependent RNA polymerase, and are translated in vivo via a subgenomic mRNA (Ding et al., *EMBO J*, 14:5762 (1995)).

Methods

Figure 3:
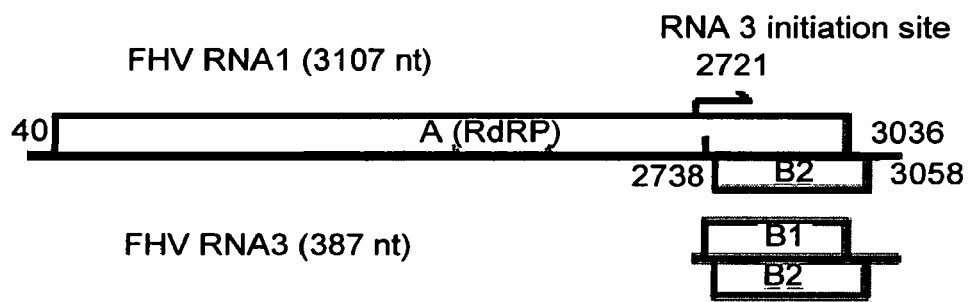
FIG. 3 illustrates the genome organization and expression of FHV RNA1 (Ball et al., in *Virus taxonomy—Seventh report of the international committee on taxonomy of viruses*. H. V. van Regenmortel et al., Eds. (Academic Press, 2000), pp. 747). RNA1 encodes protein A, which is the catalytic subunit of the viral RNA-dependent RNA polymerase. RNA3 encodes proteins B1 and B2. B1 is encoded in the same ORF as protein A whereas B2 is encoded in the +1 reading frame of protein A. The initiation codon for B1 (indicated by a vertical line) is 10 nt upstream the B2 ORF. RNA2 encodes the coat protein precursor and is replicated in trans by protein A.

Full-length cDNA of FHV RNA1, together with a tobacco ringspot virus satellite RNA ribozyme at the 3'-end (L. A. Ball, *J Virol*, 69:720 (1995)), was cloned immediately downstream of the $CuSO_4$-inducible metallothionein promoter in pMT/V5-HisA vector (Invitrogen) to give pRNA1 (see, FIG. 3). Precise fusion of the RNA1 sequence at the +1 transcriptional site was achieved by mutagenesis via PCR (Ding et al., *EMBO J*, 14:5762 (1995)).

pRNA1-ΔB2 was derived from pRNA1 and contained the two point mutations (T2739C and C2910A) described previously (L. A. Ball, *J Virol*, 69:720 (1995)) that abolished the coding potential of ORF B2 but had no effect on the overlapping ORF A in the genomic RNA or ORF B1 in RNA3. The full-length RNA3 sequence (see, FIG. 3) with the start codon of the ORF B1 changed to AGC was cloned in pMT/V5-HisA to yield pB2. The 3'-untranslated region of RNA3 up to and including the stop codon in pB2 was replaced by a sequence coding for the 6×His tag plus a stop codon at the 3'-end to give pB2/His. Plasmid transfection and subsequent transcriptional induction one day after transfection were carried out according to manufacturer's recommendation.

RNAi procedure and dsRNAs corresponding to cyclinE, GFP, AGO2, Dicer 1 and 2 were as described (Hammond et al., *Science*, 293:146 (2001); Bernstein et al., *Nature*, 411: 494 (2001); Hammond et al., *Nature*, 404:293 (2000)).

dsRNA corresponding to the 3-terminal 500 nts of FHV RNA1 was generated similarly by in vitro transcription.

Total RNAs were extracted from S2 cells two days after induction and RNA blot probed with a cDNA corresponding to the 3'-terminal 1672 nts of RNA1 (FIG. 2D).

The AGO2 probe hybridized to the central region of AGO2 mRNA that does not overlap the terminal regions targeted by dsRNAs.

FHV virion purification and infection of S2 cells were carried out as described (Friesen et al., *J. Virol.*, 42, 986 (1982)).

The riboprobe detecting the FHV-specific siRNAs was complementary to the 3'-terminal 1672 nt of RNA1 (FIG. 2A). cDNA probes used in FIG. 2B corresponded to nucleotides 2428-3002 of RNA1 and nucleotides 469-1076 of RNA2. Reproducible results were obtained from at least three independent infection/transfection experiments.

Effect of B2 Deletion on GFP Protein Expression as Detected by a *Agrobacterium* Co-Infiltration Assay The FHV B2 protein exhibited a potent silencing suppression activity (FIG. 1) in the *Agrobacterium* co-infiltration assay (Voinnet et al., *Cell*, 103:157 (2000)), established in transgenic plants expressing green fluorescent protein (GFP). Transient B2 expression prevented RNA silencing of the GFP transgene, leading to a strong and prolonged green fluorescence examined under UV illumination (FIG. 1, left), similar to suppression by the cucumoviral 2b proteins (Guo et al., *EMBO J*, 21:398 (2002); FIG. 1, right).

In contrast, a broad red fluorescent zone surrounding the infiltrated patch (FIG. 1, middle) became clearly visible six days post infiltration when the co-infiltrated transgene directed translation of neither 2b nor B2.

Confirmation of Function of B2 in Plants by Northern Blot
Overview

RNA blot hybridizations confirmed that expression of either protein was associated with high accumulation levels of the GFP mRNA. In addition, the GFP-specific siRNAs (Hamilton et al., *Science*, 286:950 (1999)) remained at extremely low levels in the leaves where there was expression of either B2 or 2b.

Methods cDNA to FHV RNA3 was cloned between the cauliflower mosaic virus 35S promoter and terminator in a binary plasmid and transformed into *A. tumefaciens* as described (Guo et al., *EMBO J*, 21:398 (2002)). 35S-B2 and 35S-B1 directed expression of protein B2 and B1, respectively, as the initiation codon of ORFB1 was changed to AGC in 35S-B2 and that of ORFB2 was changed to ACG in 35S-B1. 35S-ΔB2 did not code for any FHV proteins as initiation codons of both ORF B1 and B2 were changed to ATC. cDNAs encoding the tomato aspermy virus 2b (T2b) and its untranslatable coding sequence (TΔ2b) described previously (Li et al., *EMBO J*, 18:2683 (1999)) were similarly cloned to the binary vector to give 35S-T2b and 35S-TΔ2b. *A. tumefaciens* strain 35S-GFP (Brigneti et al., *EMBO J*, 17:6739 (1998)) was mixed with either 35S-B2, 35S-B1, 35S-ΔB2, 35S-T2b, or 35S-TΔ2b before infiltrated into the leaves of the GFP-expressing *N. benthamiana* plants.

Results

FIG. 4A shows Northern blot analysis of total RNAs extracted 3 and 6 days after infiltration with 35S-GFP alone (−; lanes 1 & 6) or plus 35S-B2 (B2; lanes 2 & 7), 35S-B1 (B1; lanes 3 & 8), 35S-Δ32 (ΔB2; lanes 4 & 9), or 35S-T2b (T2b; lanes 5 & 10). The filter was successively hybridized with probes specific for the coding sequence of GFP (upper panel) and B2 (lower panel) as described (Guo et al., *EMBO J*, 21:398 (2002)). Equivalent loading of the total plant RNA for each lane was determined by methylene blue staining of the ribosomal RNA.

FIG. 4B shows the accumulation of GFP siRNAs. siRNAs were extracted from the same samples described above and analyzed as described (Guo et al., *EMBO J*, 21:398 (2002)). Lane 11 contained three RNA species of 22, 23 and 26 nucleotides in length transcribed in vitro from linearized plasmids by T7 RNA polymerase. Note that when co-infiltrated with 35S-GFP, expression of either B2 (lanes 2 and 7) or T2b (lanes 5 and 10) was associated with high accumulation levels of the GFP mRNA in infiltrated leaves (FIG. 2A, upper panel). Further, the GFP-specific siRNAs (FIG. 2B) accumulated to high levels in the 35S-GFP infiltrated leaves (lanes 1 and 6), but remained at extremely low levels in the leaves that also expressed B2 (lanes 2 and 7) or T2b (lanes 5 and 10). In contrast, when the co-infiltrated FHV-derived transgene directed expression of no protein product (lanes 4 and 9) or the overlapping B1 (lanes 3 and 8), the accumulation of siRNAs was as high as these infiltrated with 35S-GFP alone. In addition, in vivo expression of B2, but not of B1, was correlated with the accumulation of the FHV-specific mRNA (FIG. 2A, lower panel) and the absence of the FHV-specific siRNAs, indicating that mRNA derived from the infiltrated FHV transgene was also targeted for silencing in the infiltrated leaves.

Construction and Plant Infections of CMV Chimera

B2 was able to functionally substitute for 2b of cucumber mosaic virus (CMV) in whole plant infections, as found previously for a CMV 2b homologue (Ding et al., *Proc Natl Acad Sci USA*, 93:7470 (1996)).

Infectious CMV (Q strain) plasmid DNAs, pQCD1, 2 and 3 (Ding et al., *EMBO J*, 14:5762 (1995)), were first cloned into a single binary plasmid to give pBinCMV. pBinCMV-Δ2b was obtained by replacing the 2b coding sequence in pBinCMV with a unique SmaI site. The coding sequence for B2 or T2b was then cloned to the SmaI site to give pBinCMV-B2 and pBinCMV-2b. These binary plasmids were transformed into *A. tumefaciens* and seedlings of *N. tabacum* (cv. Samsun) were inoculated by *Agrobacterium* infiltration. Four, 7 and 14 days after inoculation, total RNAs were extracted from the inoculated and systemically infected leaves and analyzed by Northern hybridizations using a $^{32}$P-labeled cDNA probe corresponding to the 3' terminal 200 nucleotides of CMV RNA 2.

The results show that the defect of virus RNA accumulation in the inoculated and systemically infected leaves, known to be associated with the deletion of 2b (Ding et al., *EMBO J*, 14:5762 (1995); Ding et al., *Proc Natl Acad Sci USA*, 93:7470 (1996)), was largely rescued by the expression of either B2 or T2b.

FHV Triggers RNA Silencing in *Drosophila* Cells

The finding that an FHV-encoded protein suppresses RNA silencing in plants indicates that it also plays a role for RNA silencing in FHV infections of animal hosts. FHV belongs to the Nodaviridae family, members of which naturally infect vertebrate and invertebrate hosts and *Drosophila* cells support complete infection cycles of FHV (Ball et al., in *Virus taxonomy—Seventh report of the international committee on taxonomy of viruses*. H. V. van Regenmortel et al., Eds. (Academic Press, 2000), pp. 747).

Figure 2:
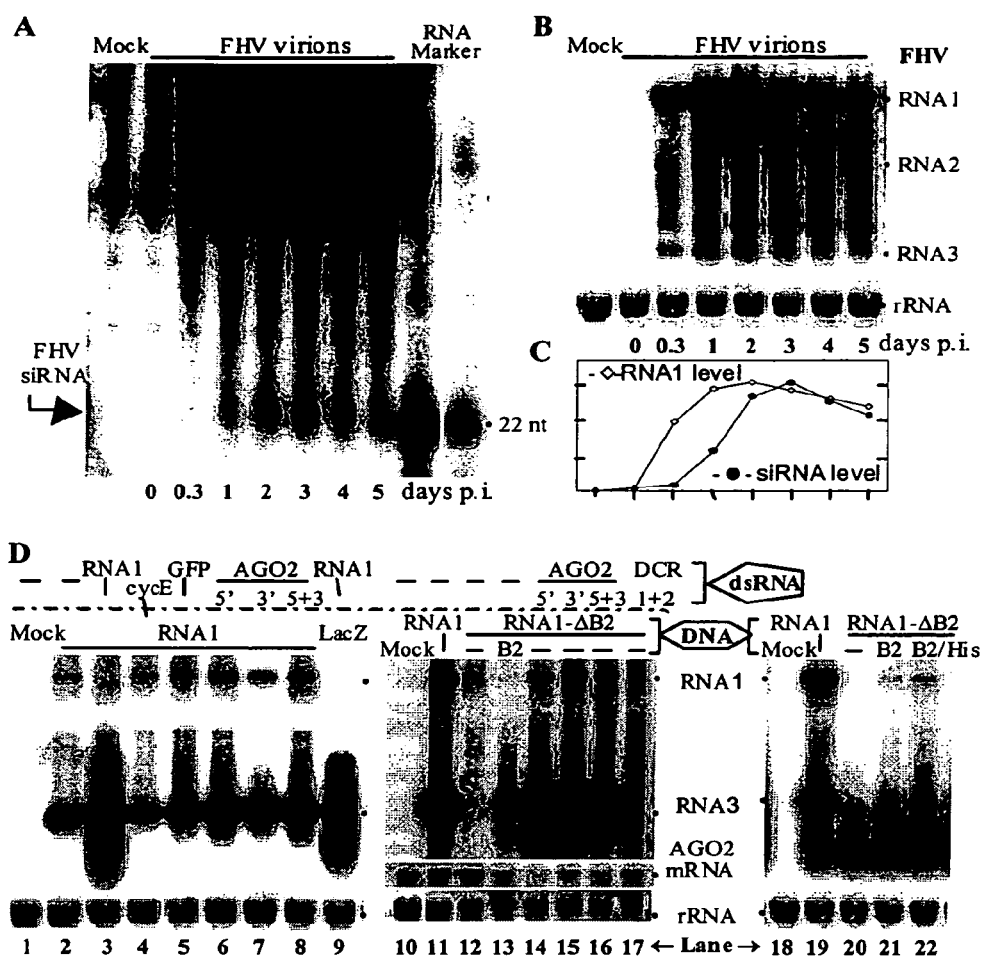
FIG. 2 illustrates induction and suppression of RNA silencing in *Drosophila* by FHV. (A to C) A time course analysis on the accumulation of FHV siRNAs (A) and RNAs 1-3 (B) in S2 cells infected with FHV virions and densitometry measurements of the accumulation levels of FHV RNA1 and siRNA are shown in (C). An RNA marker of 22 nt in length transcribed in vitro was loaded in the right lanes (A). (D) Accumulation of FHV RNAs in S2 cells transfected with pRNA1 or pRNA1-ΔB2 with or without dsRNA. dsRNA corresponding to mRNA of cyclin E (cycE), GFP and two fly DCR genes, to the 5' and 3'-terminal 1,000 nt of the AGO2 mRNA (Hammond et al., *Science*, 293:1146 (2001); Bernstein et al., *Nature*, 409:363 (2001); Hammond et al., *Nature*, 404:293 (2000)), and to the 3'-terminal 500 nt of FHV RNA1, or a B2-expressing plasmid that were co-transfected into S2 cells are indicated above each lane.

FIG. 2 shows that infection of *Drosophila* S2 cells with FHV virions results in a rapid appearance of FHV-specific siRNAs of both plus (FIG. 2A) and minus polarities. Accumulation of siRNA trailed that of FHV genomic and subgenomic RNAs (FIG. 2C), suggesting that the decreased accumulation of FHV RNAs at later stages of FHV infection (Johnson et al., *J Virol,* 73:7933 (1999); FIG. 2B) is due to FHV-specific RNA silencing.

ARGO2, Part of the RISC Complex, is a Component of the RNA Silencing Pathway in Animals To investigate this possibility, we constructed a full-length FHV RNA1 cDNA clone, pRNA1 (see, FIG. 3), which after transfection into S2 cells directed RNA1 self-replication and transcription of RNA3 (L. A. Ball, *J Virol,* 69:720 (1995)), the subgenomic mRNA for B2 (FIG. 2D, lane 2). We found that depleting the mRNA of Argonaute2 (AGO2) by RNAi, an essential component of the RISC complex (Hammond et al., *Science,* 293:146 (2001)), led to a pronounced increase (2-3 fold) in the accumulation of FHV RNAs 1 and 3 (lanes 6-8) whereas co-transfection of cyclinE or GFP dsRNAs with pRNA1 had minimal effect (lanes 4-5), indicating that a functional RNA silencing pathway naturally restricted FHV accumulation in the host cells.

Furthermore, co-transfection of pRNA1 with a dsRNA targeting the 3'-terminal 500 nucleotides of FHV RNA1 completely prevented accumulation of intact FHV RNA1 in S2 cells (lane 3). These results collectively demonstrate that FHV is both an initiator and target of RNA silencing in this animal host.

B2 is Essential for FHV Accumulation in *Drosophila* Cells

Further studies showed that B2 was essential for FHV accumulation in the *Drosophila* cells, which is in contrast to a previous study carried out in non-host mammalian cells (L. A. Ball, *J Virol,* 69:720 (1995)). A B2-knockout mutant of FHV RNA1, referred to as RNA1-ΔB2, which contains the previously described point mutations (L. A. Ball, *J Virol,* 69:720 (1995)) that converted the first and 58th codons of the B2 ORF into Ser and stop codons respectively, failed to accumulate to detectable levels after transfection into S2 cells (lanes 12 and 20).

This defect was partially trans-complemented (up to 10% of the wild type level) by co-transfection of a plasmid expressing either B2 (lanes 13 and 21) or a His-tagged B2 (lane 22). Expression of the His-tagged B2 from the co-transfected plasmid was detected in S2 cells by Western blot analysis using an antibody recognizing the His tag.

RT-PCR and sequencing revealed that the introduced mutations were stably maintained in the progeny FHV RNAs extracted from infected cells, indicating that B2 was indeed expressed from the co-transfected plasmid rather than from a revertant RNA1.

B2 Suppresses FHV RNA Silencing in *Drosophila* Cells

Significantly, accumulation of RNA1-ΔB2 in S2 cells was efficiently rescued, up to 50% of the wild type level, by co-transfection with the AGO2 dsRNAs either singly (lanes 14-15) or in combination (lane 16). However, co-transfection with dsRNAs targeting mRNAs of the two *Drosophila* Dicer genes (Bernstein et al., *Nature,* 411:494 (2001)), was not effective (lane 17) under the same conditions. This is possibly due to a more efficient mRNA depletion by RNAi for AGO2 (lanes 14-16) than Dicer (Hammond et al., *Science,* 293:146 (2001); Bernstein et al., *Nature,* 411:494 (2001)), which is required to process the input dsRNA. Notably, the level of complementation by RNAi of AGO2 was higher than that achieved by the B2-expressing plasmid (lane 13), although still less efficiently than B2 expression from wild type RNA1 (lane 10). Therefore, in the absence of B2 expression, FHV RNAs 1 and 3 accumulated to substantial levels when the RISC complex was disrupted by AGO2 depletion.

These data confirmed the previous finding (L. A. Ball, *J Virol,* 69:720 (1995)) that B2 is not required for RNA1 self-replication and indicate that the essential function of B2 for FHV infection of the S2 host cells observed in this study was to suppress RNA silencing that targeted FHV RNAs for degradation.

CONCLUSIONS

Thus, the same protein blocks RNA silencing in both animals and plants, providing the first experimental evidence for a highly conserved RNA silencing pathway in different kingdoms. Notably, FHV-B2 did not prevent initiation of virus RNA silencing (FIG. 2A) or RNAi (FIG. 2D), and thus may be functionally analogous to the plant viral 2b protein (Guo et al., *EMBO J,* 21:398 (2002)).

It is known that RNA interference operates in animals including mammals (D. Baulcombe, *Curr. Biol.,* 12:R83 (2002); Hutvagner et al., *Curr. Opin. Genet. Dev.,* 12:225 (2002); Elbashir et al., *Nature,* 411:494 (2001)). In this work, we demonstrate that infection of *Drosophila* cells with an RNA virus triggers strong virus RNA silencing and that the same virus is equipped with an effective silencing suppressor essential for infection. These data provide compelling, direct evidence that RNA silencing naturally acts as a novel adaptive antiviral defense in animal cells. The specificity mechanism of this adaptive defense is based on nucleic acid base pairing between siRNA and its target RNA (D. Baulcombe, *Curr. Biol.,* 12:R83 (2002); Hutvagner et al., *Curr. Opin. Genet. Dev.,* 12:225 (2002)), and thus is distinct from cellular and humoral adaptive immunity based on peptide recognition (J. L. Whitton, M. B. A. Oldstone, in *Fields Virology,* D. M. Knipe, P. M. Howley, Eds. (Lippincott Williams & Wilkins, 2001), vol. 1, chap. 11. [fourth edition]).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
            INFORMAL SEQUENCE LISTING
SEQ ID NO: 1: Amino acid sequence of the F protein
of Hepatitis C Virus
A R I L N L K K K T N V T P T V A H R

T S S S R V A V R S L V E F T C C R A G

A L D W V C A R R E R L P S G R N L E V

D V S L S P R L V G P R A G P G L S P G

T L G P S M A M R A A G G R D G S C L P

V A L G L A G A P Q T P G V G R A I W V

R S S I P L R A A S P T S W G T Y R S S

A P L L E A L P G P W R M A S G F W K T

A *

SEQ ID NO: 2: Nucleotide sequence of the F protein
of Hepatitis C Virus
augagcacgaauccuaaaccucaaaaaaaaaacaaacguaacac      60
caaccgucgcccacag
```

```
gacgucaaguucccggguggcggucagaucguugguggaguuua      120
cuuguugccgcgcagg ggcccuagauuggguguygcgcgcgacgagaaagacuuccgagcg     180
gucgcaaccucgaggu agacgucagccuaucccaaggcucgucggcccgagggcaggac       240
cugggcucagcccggg uacccuuggccccucuauggcaaugagggcugcggguggcggg      300
auggcuccugucuccc cguggcucucggccuagcuggggccccacagacccccggcguag     360
gucgcgcaauuugggu aaggucaucgauacccuuacgugcggcuucgccgaccucauggg     420
guacauaccgcucguc ggcgcccucuuggaggcgcugccagggcccuggcgcauggcgu      480
ccggguucuggaagac ggcgugaacuaugcaacagggaaccuuccugguugcucuuucuc     540
uaucuuccuucuggcc
```

---

What is claimed is:

1. A method for identifying a gene in an antiviral RNA silencing pathway of an animal, said method comprising:
   (a) providing an animal cell expressing a polynucleotide encoding FHV-ΔB2;
   (b) inhibiting the expression of a candidate gene in the antiviral RNA silencing pathway; and
   (c) testing for a rate or extent of FHV-ΔB2 RNA accumulation greater than that for a cell where the expression of said candidate gene in the antiviral RNA silencing pathway has not been inhibited.

2. The method of claim 1, wherein said polynucleotide encoding FHV-ΔB2 further comprises a coding sequence for a reporter molecule.

3. The method of claim 2, wherein said reporter molecule is GFP.

4. The method of claim 1, wherein the expression of said candidate gene is inhibited by RNA interference, antisense DNA, or a ribozyme.

* * * * *